United States Patent [19]

Jin

[11] Patent Number: 5,538,666
[45] Date of Patent: Jul. 23, 1996

[54] CONDUCTING POLYMERIC SIDE-CHAIN LIQUID CRYSTALS AND AN ORIENTATION LAYER USING THE SAME

[75] Inventor: Sung-ho Jin, Suwon, Rep. of Korea

[73] Assignee: Samsung Display Devices Co., Ltd., Kyungki, Rep. of Korea

[21] Appl. No.: 366,317

[22] Filed: Dec. 29, 1994

[30]     Foreign Application Priority Data

Aug. 27, 1994 [KR] Rep. of Korea .................. 94-21308

[51] Int. Cl.$^6$ .................. C07K 19/52; C07K 17/00; G02F 1/13; B32B 9/04
[52] U.S. Cl. .................. 252/299.01; 252/299.61; 252/299.66; 252/299.68; 359/99; 428/1; 428/411.1; 534/798; 549/70; 549/74
[58] Field of Search .................. 252/299.01, 299.61, 252/299.66, 299.68; 428/411.1, 414; 359/99; 525/171, 185, 256; 528/380; 534/798; 549/70, 74

[56]         References Cited

U.S. PATENT DOCUMENTS

| | | | |
|---|---|---|---|
| 4,657,694 | 4/1987 | Heeger et al. | 252/249.01 |
| 4,769,448 | 9/1988 | Heeger et al. | 252/249.0 |
| 5,278,295 | 1/1994 | Suzuki et al. | 252/219.61 |
| 5,391,622 | 2/1995 | Ho et al. | 525/171 |

OTHER PUBLICATIONS

CA 118:102517, 1992.

*Primary Examiner*—Shean C. Wu
*Attorney, Agent, or Firm*—Rothwell, Figg, Ernst & Kurz

[57]            ABSTRACT

Conducting polymeric side chain liquid crystals are prepared by incoporating liquid crystalline compounds in a main chain selected from the group consisting of acetylene derivatives and thiophene derivatives. The liquid crystal has conductivity and liquid crystallinity at the same time and is soluble in most organic solvents, giving good processability. The liquid crystals are advantageously used as a polymer membrane as well as an orientation layer.

24 Claims, 2 Drawing Sheets

FIG. 1

CONDUCTING POLYMERIC SIDE-CHAIN LIQUID CRYSTALS AND AN ORIENTATION LAYER USING THE SAME

FIELD OF THE INVENTION

The present invention relates to conducting polymeric side-chain liquid crystals and an orientation layer using the same, and particularly to conducting polymeric side-chain liquid crystals prepared by incoporating a liquid crystalline compound in electro-conducting compounds such as acetylene, thiophene derivatives, and an orientation layer using the same.

BACKGROUND OF THE INVENTION

Recently, research on side-chain liquid crystals which has applicability for photo-electric devices is being widely progressed. Most of the side-chain liquid crystals are limited to the compounds such as siloxane derivatives, acrylate derivatives, methacrylate derivatives, etc., all of which are known to have no conductivity.

Moreover, the vast majority of conventional conducting polymer is insoluble in organic solvents and their oxidation stability with respect to the air and thermal properties are not good. Especially, processability is not good. In the case of using conducting monomers such as thiophene, pyrrole, paraphenylene, etc., conducting polymers insoluble in organic solvents were prepared owing to a problem with the synthetic method therefor. Recently, by incoporating a thiophene derivative having a great number of carbon atoms at the 3-position of the thiophene, a conducting polymer soluble in organic solvents was prepared.

However, this kind of organic solvent-soluble conducting monomer is somewhat difficult to synthesize. Also, electric polymerization should be applied (see J. R. Reynolds, Macromolecules, 1991, Vol. 24, p678; and Japanese Patent Laid-open Publication No. hei 3-086721).

Meanwhile, a side-chain liquid crystal polymer is a material having high applicability as a membrane which can control the permeation of pharmaceuticals or gas. The membrane can selectively permeate special properties and/or materials to the flow of heat or material. A method for the separation of gases using the membrane is proceeded using the difference of the permeation velocity of each of mixed gases to pass through the semi-permeable membrane.

Recently, research has been actively concentrated on a membrane separation process among various separation processes and particularly on a process for an oxygen enrichment membrane. The oxygen-enriched air is used for a combustion system or in the medical field, while nitrogen-enriched air is industrially used for cleaning ambient air in connection with semiconductor manufacturing facilities.

Requirements for the oxygen enrichment membrane are as follows.

1. high permeability for oxygen (high $P_{O2}$)
2. high separability for oxygen (high $P_{O2}/P_{N2}$)
3. thermodynamic stability and durability The permeability of the gases for a non-porous polymer membrane depends on the phase of the polymer, i.e., whether rubber phase or glass phase. The polymer of the rubber phase shows fast reaction on the gases dissolved in the membrane, as a result of the flexible backbone. However, the problem of the difficulty in formation of a thin film exists.

A polymer which is capable of manufacture into a thin film using an organic solvent and has high gas permeability can be manufactured by employing a rigid backbone and a flexible side chain poly(dimethylsiloxane) (PMDS) or poly (1-(trimethylsilyl)-1 -propyne), which is used as an oxygen enrichment membrane among the known polymers, shows high permeability. However, drawbacks such as low selectivity or difficulty in manufacturing remain.

The inventor of the present invention has performed research on preparing a novel conducting polymeric side-chain liquid crystal by incoporating liquid crystalline compounds in a conducting monomer such as a diacetylene derivative, thiophene derivative, pyrrole derivative, aniline derivative, etc., using various synthetic methods, to carry out a study on the relation between conductivity and liquid crystallinity.

SUMMARY OF THE INVENTION

An object of the present invention is to provide conducting polymeric side-chain liquid crystals which can be used for an organic solvent-soluble orientation material which can be applied to a display, gas separation membrane, etc.

Another object of the present invention is to provide an orientation layer formed by using the conducting polymeric side-chain liquid crystals of the present invention.

To accomplish the first object of the present invention, there is provided in the present invention conducting polymeric side-chain liquid crystals prepared by incoporating liquid crystalline compounds in a main chain selected from the group consisting of acetylene derivatives and thiophene derivatives.

The other object of the present invention is accomplished by an orientation layer manufactured by using the conducting polymeric side-chain liquid crystals.

Preferably, the liquid crystal is at least one compound selected from the group consisting of the following liquid crystals having the structures of (I), (II), polymer compounds thereof, (III), (IV), and mixtures thereof.

wherein $R_1$ is H or

X is one selected from the group consisting of $CO_2(CH_2)_mO$, $CH_2O(CH_2)_mO$, $CO_2(CH_2CH_2O)_m$ and $CH_2O(CH_2CH_2O)_m$, (m is 1–6), Y is one of direct connection, $CO_2$, CH=N or N=N, $R_2$ is $O(CH_2)_pCH_3$ (p is 0–6) or CN, and n i s an integer.

Copolymers of the compounds (I) and (II), or a mixture of (III) and (IV) may also be included in the liquid crystals of the present invention.

BRIEF DESCRIPTION OF THE DRAWINGS

The above objects and advantages of the present invention will become more apparent by describing in detail a preferred embodiment thereof with reference to the attached drawings in which.

DETAILED DESCRIPTION OF THE INVENTION

Since the liquid crystals of the present invention show liquid crystalline characteristics as well as conductivity, the relation between the conductivity and liquid crystalline characteristic can be determined and an organic solvent-soluble functional polymer can be obtained.

Conducting polymeric side-chain liquid crystals are prepared from monomers of diacetylene derivatives using a transition metal catalyst such as $WCl_6$ or $MoCl_5$ under various synthetic conditions in the present invention. The yield is as high as 80% or more. Conducting polymeric side-chain liquid crystals are prepared from thiophene derivatives, through a chemical synthetic method and using $FeCl_3$ as a catalyst.

The preferred embodiments of the present invention will be described in detail below.

EXAMPLE 1 synthesis of 4-methoxy-4'-hydroxybiphenyl (1)

75 g (0.40 mol) of 4,4'-dihydroxybiphenyl was dissolved in 400 ml of a 10% aqueous sodium hydroxide solution in a water bath. 50.4g (0.40 mol) of dimethyl sulfate was dropwisely added at 0° C. for three hours. When a milky solid was formed, the solid was filtered using a vacuum filter and the filtered solid was washed using 500 ml of the 10% aqueous sodium hydroxide solution. The solid was dissolved in boiling water and the remaining residue was filtered out using a vacuum filter. A 20% hydrochloric acid was added to the solution, to acidify the solution at 70° C. The thus-formed solid was filtered and recrystallized in ethanol. Here, yield was 55% and the melting point was 183° C. The chemical shift on the $^1$-H-NMR spectrum of the produced compound was: $^1$H-NMR ($CDCl_3$); δ(ppm) 3.82(s, 3H), 6.86(d, 2H), 6.93(d, 2H), 7.40(d, 2H) and 7.45(d,2H)

EXAMPLE 2 synthesis of 4-methoxy-4'- (6-hydroxyhexyloxy) biphenyl (2)

20 g (0.1 mol) of 4-methoxy-4'-hydroxybiphenyl and 6.2 g (0.11 mol) of potassium hydroxide were dissolved in 150 ml of hot ethanol and the mixture was stirred for one hour. 15 g (0.11 mol) of 6-chloro-1-hexanol was added to the mixture and the reaction mixture was refluxed for twenty hours. The solution was diluted by adding distilled water and was washed with aqueous potassium hydroxide. The product was separated using column chromatography and was recrystallized using ethanol. The yield of the product was 70% and the melting point was 135° C. The chemical shift on the $^1$H-NMR spectrum of the produced compound was: $^1$H-NMR ($CDCl_3$); δ(ppm) 1.2~1.8 (m, 8H) , 3.37(t, 2H) , 3.77(s, 3H) , 3.97(t, 2H) and 6.94~7.45 (d, 8H)

EXAMPLE 3 synthesis of 3- (6-bromohexyloxy) methylthiophene (3)

22.89 (0.2 mol) of 3-thiophenemethanol reacted with sodium hydride in tetrahydrofuran (THF) to produce sodium salt. The solution was stirred for six hours at 40° C. and a catalytic amount of potassium hydride was added thereto. The reaction mixture was dropwisely added to 97.6 g (0.4 mol) of 1,6-dibromohexane dissolved in 200 ml tetrahydrofuran for ten minutes and the mixture was stirred to proceed reaction for twelve hours at an ambient temperature. The solvent was evaporated by vacuum distillation. 500 ml of distilled water was added to the residue and the organic layer was extracted three times using 50 ml of methylene chloride. The solution was dried using magnesium sulfate and the solvent was vacuum-distilled (140° C./0.2 mmHg). The yield was 65%. The chemical shift on the $^1$H-NMR spectrum of the produced compound was: $^1$H-NMR (CDCl$_3$); δ(ppm) 1.5 (m, 8H) , 3.3 (m, 4H) , 4.4 (s, 2H) , 7.1(m, 3H) and 7.1 (m, 3H)

EXAMPLE 4 synthesis of 4-methoxy-4'-[2 bis(ethyleneoxy)ethanol] biphenyl (4)

10g (0.05 mol) of 4-methoxy-4'-hydroxybiphenyl and 3.4 g (0.06 mol) of potassium hydroxide were dissolved in 200 ml of ethanol. 10.1 g (0.06 mol) of 2-[2-(2-chloroethoxy)ethoxy]ethanol was added to the solution and the mixture was refluxed for fifteen hours. Distilled water was added to the reaction mixture, the thus-obtained precipitate was filtered, and the precipitate was washed using aqueous sodium hydroxide solution. The product was separated using column chromatography and recrystallized using ethanol. The chemical shift on the $^1$H-NMR spectrum of the produced compound was: $^1$H-NMR (CDCl$_3$); δ(ppm) 3.52(s,4H), 3.62(s,4H), 3.83(m, 5H), 4.13(t,2H) and 7.0~7.57(d,8H), a yield of 73% and a melting point of 96°–98° C.

EXAMPLE 5 synthesis of 4-[(4-methoxyphenyl)azo]phenol (5)

3.9 g (0.02 mol) of p-anisidine was dissolved in distilled water and 8.8 g (49% aqueous solution, 0.05 mol) of fluoroboric acid was slowly added. The reaction mixture was cooled for 30 minutes, and 1.45 g (0.02 mol) of sodium nitrite, 4.3 g (0.045 mol) of phenol and 6.8 g of sodium acetate were added thereto. The reaction mixture was acidified with hydrochloric acid and the obtained precipitate was separated and recrystallized using ethanol. Here, a yield of 97% was obtained and the melting point was 112°–113° C.

EXAMPLE 6

4-[(methoxyphenyl)azo 4'-(2-bis(ethyleneoxy)ethanol)] phenyl (6)

14.9 g (0.12 mol) of 2-[2-(2-chloroethoxy)ethoxy]ethanol was dissolved in 50 ml of ethanol. 5.6 g (0.10 mol) of potassium hydroxide was added to this solution, 22.8 g (0.10 mol) of 4-[(4-methoxyphenyl)azo] phenol and a catalytic amount of potassium iodide in 500 ml of ethanol solution was added. The reaction mixture was refluxed for sixteen hours and was acidified using hydrochloric acid. The solvent was distilled. The residue was dissolved in chloroform and was washed using distilled water. The solution was dried using anhydrous magnesium sulfate and the solvent was distilled off. The product was separated using column chromatography and recrystallized using methanol. The chemical shift on the $^1$H-NMR spectrum of the produced compound was: $^1$H-NMR (CDCl$_3$); δ(ppm) 3.67~4.26(m, 15H) and 6.96~7.92(m, 8H)

EXAMPLE 7 synthesis of 4-methoxy-4'-hexyloxybiphenyl dipropargyl acetate (M-1)

Nitrogen gas was injected in a 150 ml container and 100 ml of THF was added. Then, 15 g (0.05 mol) of the compound (2) and 6.5 g (0.065 mol) of triethylamine was dropwisely added to the solvent, to obtain a mixture. 6.4 g (0.045 mol) of dipropargyl acetyl chloride was diluted in 100 ml of tetrahydrofuran and the solution was dropwisely added to the mixture for two hours. After the reaction was completed, distilled water was added and the precipitate was filtered. The product was separated using column chromatography and recrystallized using methanol. The yield was 76%.

EXAMPLE 8 synthesis of 4-[(4-methoxyphenyl)azo-4'-{2bis(ethyleneoxy) ethanol}] phenyl dipropargyl acetate (M-2)

10.8g (0.03 mol) of the compound (6) and 3.2 g (0.032 mol) of triethylamine were dissolved in 100 ml of THF. Then, 4.5 g (0.032 mol) of dipropargyl acetyl chloride was dropwisely added to the solution and the reaction was proceeded for five hours. The reaction mixture was added to distilled water and the precipitate was separated. The product was separated using column chromatography and recrystallized using methanol. The yield was 89%.

EXAMPLE 9 synthesis of 3- (4-methoxy-4' -hydroxybiphenyl) oxy methylthiophene (M-3)

10g (0.05 mol) of 4-methoxy-4'-hydroxybiphenyl and 21 g (0.05 mol) of potassium carbonate were added to 200 ml of dimethylformamide. Then, 13.9 g (0.05 mol) of 3-(6-bromohexyloxy)methylthiophene was dropwisely added to the mixture. The reaction mixture was stirred at 80° C. for 24 hours. The solution was added to 300 ml of distilled water and the solid was separated by filtering. The product was recrystallized using 200 ml of methanol to produce the compound M-3 with an 85% yield. The melting point was 95°-97° C. and the chemical shift on the $^1$H-NMR spectrum of the produced compound was: $^1$H-NMR (CDCl$_3$); δ(ppm) 1.5–2.0(m, 8H), 3.5(t,2H), 4.0–4.2 (m, 5H) , 4.5 ( s, 2H) and 7.0–7.5 (m, 8H)

EXAMPLE 10 synthesis of 3- (4-cyano-4'-hexyloxybiphenyl) oxymethylthiophene (M-4)

9.8 g (0.05 mol) of 4-cyano-4'-hexyloxybiphenyl and 21 g (0.05 mol) of potassium carbonate were added to 200 ml of dimethylformamide. Then, 13.9 g (0.05 mol) of 3-(6-bromohexyloxy)methylthiophene was dropwisely added to the mixture and the thus-obtained mixture was stirred at 80° C. for 24 hours. The reactant was added to 300 ml of distilled water and was extracted three time using 50 ml of diethyl-ether. The solution was dried using magnesium sulfate. The solvent was vacuum-distilled and the residue was recrystallized using methanol to obtain a M-4 compound with a 51% yield. The chemical shift on the $^1$H-NMR spectrum of the produced compound was: $^1$H-NMR (CDCl$_3$); δ(ppm) 1.8–2.6 (m, 8H) , 3.4 (t, 2H) , 4.0 (t, 3H) , 4.4(s, 2H) and 6.8–7.6 (m, 8H)

The phase transition temperatures of the diacetylene and thiophene liquid crystals (M-1, 2,3,4) according to the examples and polymers thereof (P-1,2,3,4) are as follows.

M-1: K 75 S 106 i
M-2: K 60 i
M-3: K 10 S 102 i
M-4: K -30 S 33 i
P-1: K 92 S 119 i
P-2: K 80 i
P-3: crystal
P-4: crystal Here, K represents crystalline state, S represents smectic phase and i represents isotropic liquid. That is, in M-1,2,3,4 and P-1, the smectic phase appears over a wide temperature range and the nematic phase does not appear at all.

The polymers were synthesized as follows.

First, a catalyst was prepared under a nitrogen atmosphere. Halogen salt of a transition metal catalyst and a organic metal compound were dissolved in an organic solvent to give a solution having a 0.2M concentration. The solvent, catalyst and co-catalyst (as necessary) were placed into a 20 ml container, and the mixture was aged at 30° C. for fifteen minutes.

A monomer solution and the catalyst were added to the polymerization container. Reaction was proceeded at 60° C. for 24 hours. To complete the reaction, MeOH was added and the polymer was dissolved in 1,4-dioxane. The excess MeOH was poured into the solution. The thus-obtained precipitate was filtered, dried at 40° C. for 24 hours under vacuum, and weighed to calculate the yield.

Figure 1:
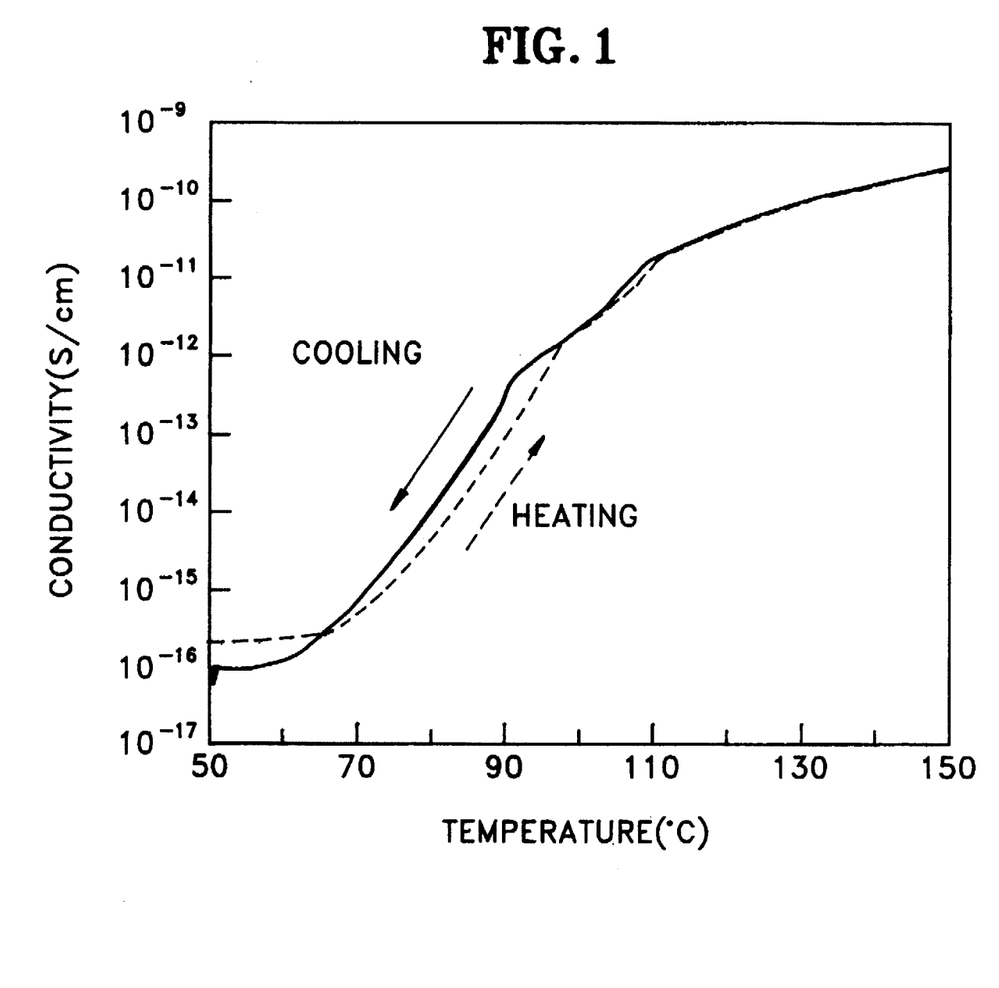
FIG. 1 is a graph representing conductivity according to the temperature of the conducting polymeric liquid crystal (P-1) which is not doped with $I_2$, among the liquid crystals of the present invention.

FIG. 1 is a graph representing conductivity according to the temperature of the conducting polymeric liquid crystal (P-1 ) which is not doped with I$_2$, among the liquid crystals of the present invention. The conductivities of most of the conducting polymers are increased and then abruptly decreased according to the increase of the temperature. However, the conductivities of the compounds of the present invention are increased and then abruptly increased in the temperature range of appearing liquid crystalline characteristic according to the increase of the temperature. The abrupt increase in conductivity is considered as follows. When the compounds show liquid crystalline characteristics, the orientation of the main chain of the polymer is affected, to increase the conductivity. Moreover, since the polymers are organic solvent-soluble, better physical properties during processing can be obtained when compared with the conventional conducting polymers of thiophene, pyrrole, etc.

EXAMPLE 11

To test gas permeability, the prepared P-2 was dissolved in ethyl acetate to form a thin film. The coefficient of oxygen permeability for the polymer was 35° C. barrer (1 barrer =$1\times10^{-10}$cm$^{-3}$ (STP); cm cm$^{-2}$S$^{-2}$cmHg$^{-1}$) for $P_{O2}$. The separation factor of oxygen and nitrogen, $P_{O2}/P_{N2}$, was detected as 3.2. These results are superior to that for the conventional poly(dipropargyl malonate) ($P_{O2}$=3.3 barrer, $P_{O2}/P_{N2}$=1.8).

EXAMPLE 12

Forming of orientation layer and baking

Purified P-2 was dissolved in ethyl acetate in 3wt % concentration. This solution was spin-coated on upper and lower substrates coated with a transparent conducting layer. The solvent was completely removed by heating at 100° C. for ten minutes.

Orientation treatment and joining of substrates

The upper and lower substrates were rubbed and a sealant was printed on one substrate, while 1.5 μm spacers were coated on the other substrate to maintain a cell gap. The upper and the lower substrates were joined and uniform pressure and heat was applied to the joined substrates, to manufacture an empty cell.

Figure 2:
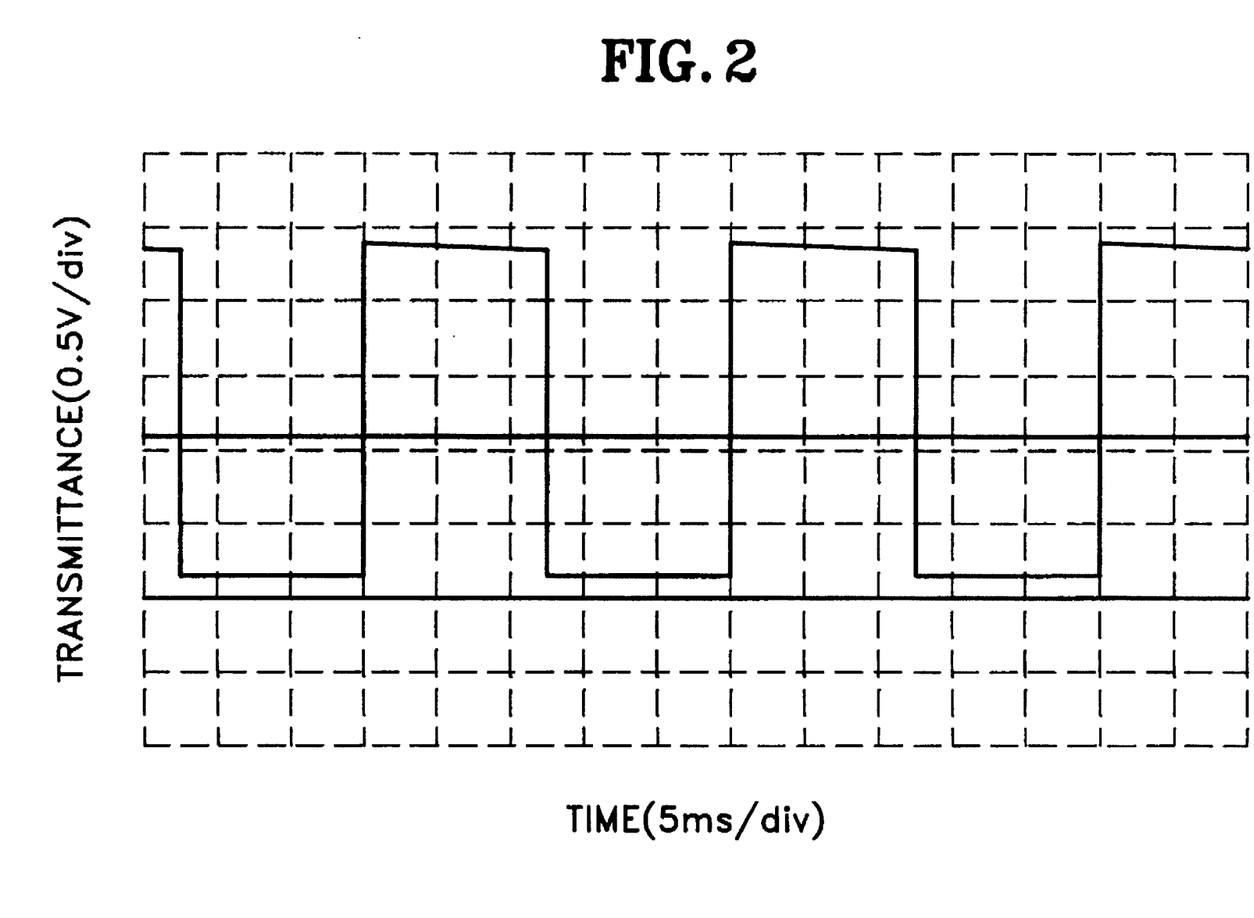
FIG. 2 represents the electro-optic characteristic of the liquid crystal display device manufactured by example 12 when the liquid crystal is orientated.

Injection of liquid crystal and detection of electro-optic characteristic T-250 liquid crystal manufactured by Hoechst Co., was injected isotropically into the space between the orientation layers and was cooled to an ambient temperature at a rate of 1° C. per minute. The orientation state was observed under a cross nicol. FIG. 2 represents the electro-optic characteristic of the liquid crystal display device manufactured by example 12 when the liquid crystal is orientated. The pulse height was +20 V, pulse width was 50 μs and the frequency was 60 Hz. From this figure, it is known that the black state and white state of the cell are changed periodically and repeatedly as the polarity of the applied voltage changes. This means that the liquid crystalline compounds of the present invention are soluble in a general organic solvent and when manufacturing an orientation layer using the compounds, processability is good and a thin film can be advantageously formed. The thus-formed orientation layer has good optical memory effect. That is, the conducting polymeric side-chain liquid crystal of the present invention is suitable as a material for manufacturing an orientation layer.

As described above, the liquid crystals of the present invention are conducting polymeric side-chain liquid crystals which can be advantageously applied as an orientation layer of a liquid crystal display device or as a polymer membrane for gas separation.

What is claimed is:

1. A conductive liquid crystalline polymer, wherein the polymer has the formula wherein $R_1$ is H or X is $CO_2(CH_2)_mO$, $CH_2O(CH_2)_mO$, $CO_2(CH_2CH_2O)_m$ or $CH_2O(CH_2CH_2O)_m$ where m is 1 to 6, Y is a direct bond, $CO_2$, CH=N or N=N, $R_2$ is CN or $O(CH_2)_pCH_3$ where p is 0 to 6, and n is a positive integer.

2. A conductive liquid crystalline polymer, wherein the polymer is a mixture of and wherein $R_1$ is H or X is $CO_2(CH_2)_mO$, $CH_2O(CH_2)_mO$, $CO_2(CH_2CH_2O)_m$ or $CH_2O(CH_2CH_2O)_m$ where m is 1 to 6, Y is a direct bond, $CO_2$, CH=N or N=N, $R_2$ is CN or $O(CH_2)_pCH_3$ where p is 0 to 6, and n is a positive integer.

3. A conductive liquid crystalline polymer, wherein the polymer is made from a monomer of the formula

4. A conductive liquid crystalline polymer, wherein the polymer is made from a monomer of the formula

5. A conductive liquid crystalline polymer, wherein the polymer is made from a monomer of the formula

6. A conductive liquid crystalline polymer, wherein the polymer is made from a monomer of the formula 7. An orientation layer for use in a liquid crystal display device comprising a conductive liquid crystalline polymer, wherein the polymer has the formula wherein $R_1$ is H or X is $CO_2(CH_2)_mO$, $CH_2O(CH_2)_mO$, $CO_2(CH_2CH_2O)_m$ or $CH_2O(CH_2CH_2O)_m$ where m is 1 to 6, Y is a direct bond, $CO_2$, CH=N or N=N, $R_2$ is CN or $O(CH_2)_pCH_3$ were p is 0 to 6, and n is a positive integer.

8. An orientation layer for use in a liquid crystal display device comprising a conductive liquid crystalline polymer, wherein the polymer is a mixture of and wherein $R_1$ is H or X is $CO_2(CH_2)_mO$, $CH_2O(CH_2)_mO$, $CO_2(CH_2CH_2O)_m$ or $CH_2O$ $(CH_2CH_2O)_m$ were m is 1 to 6, Y is a direct bond, $CO_2$, CH=N or N=N, $R_2$ is CN or $O(CH_2)_pCH_3$ where p is 0 to 6, and n is a positive integer.

9. An orientation layer for use in a liquid crystal display device comprising a conductive liquid crystalline polymer, wherein the polymer is made from a monomer of the formula

10. An orientation layer for use in a liquid crystal display device comprising a conductive liquid crystalline polymer, wherein the polymer is made from a monomer of the formula

11. An orientation layer for use in a liquid crystal display device comprising a conductive liquid crystalline polymer, wherein the polymer is made from a monomer of the formula

12. An orientation layer for use in a liquid crystal display device comprising a conductive liquid crystalline polymer, wherein the polymer is made from a monomer of the formula 13. A polymer membrane for use in separating gases comprising a conductive liquid crystalline polymer, wherein the conductive liquid crystalline polymer has the formula where $R_1$ is H or X is $CO_2(CH_2)_mO$, $CH_2O(CH_2)_mO$, $CO_2(CH_2CH_2O)_m$ or $CH_2O(CH_2CH_2O)_m$ were m is 1 to 6, Y is a direct bond, $CO_2$, CH=N or N=N, $R_2$ is CN or $O(CH_2)_pCH_3$ were p is 0 to 6, and n is a positive integer.

14. A polymer membrane for use in separating gases comprising a conductive liquid crystalline polymer, wherein the conductive liquid crystalline polymer is a mixture of and wherein $R_1$ is H or X is $CO_2(CH_2)_mO$, $CH_2O(CH_2)_mO$, $CO_2(CH_2CH_2O)_m$ or $CH_2O(CH_2 CH_2O)_m$ were m is 1 to 6, Y is a direct bond, $CO_2$, CH=N or N=N, $R_2$ is CN or $O(CH_2)_pCH_3$ were p is 0 to 6, and n is a positive integer.

15. A polymer membrane for use in separating gases comprising a conductive liquid crystalline polymer, wherein the conductive liquid crystalline polymer is made from a monomer of the formula

16. A polymer membrane for use in separating gases comprising a conductive liquid crystalline polymer, wherein the conductive liquid crystalline polymer is made from a monomer of the formula

17. A polymer membrane for use in separating gases comprising a conductive liquid crystalline polymer, wherein the conductive liquid crystalline polymer is made from a monomer of the formula

18. A polymer membrane for use in separating gases comprising a conductive liquid crystalline polymer, wherein the conductive liquid crystalline polymer is made from a monomer of the formula 19. A liquid crystal display device comprising an orientation layer comprising a conductive liquid crystalline polymer, wherein the polymer has the formula wherein $R_1$ is H or

X is $CO_2(CH_2)_mO$, $CH_2O(CH_2)_mO$, $CO_2(CH_2CH_2O)$ or $CH_2O(CH_2CH_2O)_m$ where m is 1 to 6, Y is a direct bond, $CO_2$, CH=N or N=N, $R_2$ is CN or $O(CH_2)_pCH_3$ where p is 0 to 6, and n is a positive integer.

20. A liquid crystal display device comprising an orientation layer comprising a conductive liquid crystalline poly- mer, wherein the polymer is a mixture of and wherein $R_1$ is H or

X is $CO_2(CH_2)_mO$, $CH_2O(CH_2)_mO$, $CO_2(CH_2CH_2O)_m$ or $CH_2O(CH_2CH_2O)_m$ were m is 1 to 6, Y is a direct bond, $CO_2$, CH=N or N=N, $R_2$ is CN or $O(CH_2)_pCH_3$ where p is 0 to 6, and n is a positive integer.

21. A liquid crystal display device comprising an orientation layer comprising a conductive liquid crystalline polymer, wherein the polymer is made from a monomer of the formula

22. A liquid crystal display device comprising an orientation layer comprising a conductive liquid crystalline polymer, wherein the polymer is made from a monomer of the formula 23. A liquid crystal display device comprising an orientation layer comprising a conductive liquid crystalline polymer, wherein the polymer is made from a monomer of the formula 24. A liquid crystal display device comprising an orientation layer comprising a conductive liquid crystalline polymer, wherein the polymer is made from a monomer of the formula

* * * * *